United States Patent
Naasani (10) Patent No.: US 11,053,436 B2
(45) Date of Patent: *Jul. 6, 2021

(54) SURFACE MODIFIED NANOPARTICLES (71) Applicant: Nanoco Technologies, Ltd., Manchester (GB)

(72) Inventor: Imad Naasani, Manchester (GB)

(73) Assignee: Nanoco Technologies, Ltd., Manchester (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/870,146

(22) Filed: May 8, 2020

(65) Prior Publication Data

US 2020/0263086 A1 Aug. 20, 2020

Related U.S. Application Data

(60) Continuation of application No. 16/442,060, filed on Jun. 14, 2019, now Pat. No. 10,669,475, which is a continuation of application No. 15/831,019, filed on Dec. 4, 2017, now Pat. No. 10,377,944, which is a continuation of application No. 14/832,631, filed on Aug. 21, 2015, now Pat. No. 9,840,664, which is a division of application No. 13/723,418, filed on Dec. 21, 2012, now Pat. No. 9,115,097.

(60) Provisional application No. 61/579,440, filed on Dec. 22, 2011.

(51) Int. Cl.
| | |
|---|---|
| *C09K 11/06* | (2006.01) |
| *C09K 11/62* | (2006.01) |
| *H01L 33/50* | (2010.01) |
| *C09K 11/56* | (2006.01) |
| *C09K 11/70* | (2006.01) |
| *C07D 251/70* | (2006.01) |
| *B82Y 30/00* | (2011.01) |
| *B82Y 40/00* | (2011.01) |
| *C09K 11/02* | (2006.01) |
| *C07F 7/08* | (2006.01) |
| *B82Y 20/00* | (2011.01) |

(52) U.S. Cl.
CPC .............. *C09K 11/06* (2013.01); *B82Y 30/00* (2013.01); *B82Y 40/00* (2013.01); *C07D 251/70* (2013.01); *C07F 7/087* (2013.01); *C09K 11/025* (2013.01); *C09K 11/565* (2013.01); *C09K 11/623* (2013.01); *C09K 11/70* (2013.01); *H01L 33/502* (2013.01); *H01L 33/507* (2013.01); *B82Y 20/00* (2013.01); *C09K 2211/1059* (2013.01); *C09K 2211/1088* (2013.01); *Y10S 977/774* (2013.01)

(58) Field of Classification Search
CPC .... C07D 251/70; C09K 11/06; C09K 11/623; C09K 11/70; C09K 11/565; C09K 11/025; H01L 33/502; H01L 33/507
USPC ............. 544/200; 252/301.56; 977/779, 810, 977/844, 902

See application file for complete search history.

(56) References Cited

U.S. PATENT DOCUMENTS

| | | | | |
|---|---|---|---|---|
| 6,649,138 | B2 * | 11/2003 | Adams | C09K 11/02 |
| | | | | 423/403 |
| 7,108,915 | B2 * | 9/2006 | Adams | B82Y 15/00 |
| | | | | 428/403 |
| 7,147,917 | B2 * | 12/2006 | Adams | B82Y 15/00 |
| | | | | 428/403 |
| 8,158,194 | B2 * | 4/2012 | Adams | B82Y 15/00 |
| | | | | 427/212 |
| 9,115,097 | B2 * | 8/2015 | Naasani | C09K 11/06 |
| 9,174,187 | B2 * | 11/2015 | Tulsky | B01J 13/14 |
| 9,476,885 | B2 * | 10/2016 | Tulsky | G01N 33/588 |
| 9,840,664 | B2 * | 12/2017 | Naasani | H01L 33/502 |
| 10,377,944 | B2 * | 8/2019 | Naasani | C09K 11/623 |
| 10,669,475 | B2 * | 6/2020 | Naasani | B82Y 30/00 |

* cited by examiner

*Primary Examiner* — Emily A Bernhardt
(74) *Attorney, Agent, or Firm* — Blank Rome LLP (57) ABSTRACT

Surface-modified nanoparticles are produced by associating ligand interactive agents with the surface of a nanoparticle. The ligand interactive agents are bound to surface modifying ligands that are tailored to impart particular solubility and/or compatibility properties. The ligand interactive agents are crosslinked via a linking/crosslinking agent. The linking/crosslinking agent may provide a binding site for binding the surface modifying ligands to the ligand interactive agents.

20 Claims, 8 Drawing Sheets

SURFACE MODIFIED NANOPARTICLES

CROSS-REFERENCE TO RELATED APPLICATIONS

This application is a continuation of U.S. application Ser. No. 16/442,060, filed Jun. 14, 2019, which is a continuation of U.S. application Ser. No. 15/831,019, filed Dec. 4, 2017 and issued as U.S. Pat. No. 10,377,944, which is a continuation of U.S. application Ser. No. 14/832,631, filed Aug. 21, 2015 and issued as U.S. Pat. No. 9,840,664, which is a divisional of U.S. application Ser. No. 13/723,418, filed on Dec. 21, 2012 and issued as U.S. Pat. No. 9,115,097, which claims the benefit of U.S. Provisional Application No. 61/579,440, filed Dec. 22, 2011. The contents of each of these applications are incorporated by reference herein in their entirety.

BACKGROUND OF THE DISCLOSURE

A. Nanoparticles

There has been substantial interest in the preparation and characterization of compound semiconductors consisting of particles with dimensions in the order of 2-100 nm, often referred to as quantum dots and/or nanoparticles. These studies have focused mainly on the size-tunable electronic, optical and chemical properties of nanoparticles. Semiconductor nanoparticles are gaining substantial interest due to their applicability for commercial applications as diverse as biological labeling, solar cells, catalysis, biological imaging, and light-emitting diodes.

Two fundamental factors, both related to the size of the individual semiconductor nanoparticle, are primarily responsible for their unique properties. The first is the large surface-to-volume ratio: as a particle becomes smaller, the ratio of the number of surface atoms to those in the interior increases. This leads to the surface properties playing an important role in the overall properties of the material. The second factor is that, with many materials including semiconductor nanoparticles, the electronic properties of the material change with size. Moreover, because of quantum confinement effects, the band gap typically gradually becomes larger as the size of the nanoparticle decreases. This effect is a consequence of the confinement of an 'electron in a box,' giving rise to discrete energy levels similar to those observed in atoms and molecules, rather than a continuous band as observed in the corresponding bulk semiconductor material. Semiconductor nanoparticles tend to exhibit a narrow bandwidth emission that is dependent upon the particle size and composition of the nanoparticle material. The first excitonic transition (band gap) increases in energy with decreasing particle diameter.

Semiconductor nanoparticles of a single semiconductor material, referred to herein as "core nanoparticles," along with an outer organic passivating layer, tend to have relatively low quantum efficiencies due to electron-hole recombination occurring at defects and dangling bonds situated on the nanoparticle surface that can lead to non-radiative electron-hole recombinations.

One method to eliminate defects and dangling bonds on the inorganic surface of the quantum dot is to grow a second inorganic material, typically having a wider band-gap and small lattice mismatch to that of the core material, on the surface of the core particle, to produce a "core-shell" particle. Core-shell particles separate carriers confined in the core from surface states that would otherwise act as non-radiative recombination centers. One example is ZnS grown on the surface of CdSe cores. Another approach is to prepare a core-multi shell structure where the "electron-hole" pair is completely confined to a single shell layer consisting of a few monolayers of a specific material such as a quantum dot-quantum well structure. Here, the core is of a wide bandgap material, followed by a thin shell of narrower bandgap material, and capped with a further wide bandgap layer. An example is CdS/HgS/CdS grown using substitution of Hg for Cd on the surface of the core nanocrystal to deposit just a few monolayers of HgS that is then over grown by monolayers of CdS. The resulting structures exhibit clear confinement of photo-excited carriers in the HgS layer.

The most studied and prepared semiconductor nanoparticles have been II-VI materials, for example, ZnS, ZnSe, CdS, CdSe, and CdTe, as well as core-shell and core-multi shell structures incorporating these materials. Other semiconductor nanoparticles that have generated considerable interest include nanoparticles incorporating III-V and IV-VI materials, such as GaN, GaP, GaAs, InP, and InAs. Methods of synthesizing core and core-shell nanoparticles are disclosed, for example, in co-owned U.S. Pat. Nos. 6,379,635, 7,803,423, 7,588,828, 7,867,556, and 7,867,557. The contents of each of the forgoing patents are hereby incorporated by reference, in their entirety.

B. Surface Modification

Many applications of nanoparticles require that the semiconductor nanoparticle be compatible with a particular medium. For example, some biological applications such as fluorescence labeling, in vivo imaging and therapeutics require that the nanoparticles be compatible with an aqueous environment. For other applications, it is desirable that the nanoparticles be dispersible in an organic medium such as aromatic compounds, alcohols, esters, or ketones. For example, ink formulations containing semiconductor nanoparticles dispersed in an organic dispersant are of interest for fabricating thin films of semiconductor materials for photovoltaic (PV) devices.

A particularly attractive potential field of application for semiconductor nanoparticle is in the development of next generation light-emitting diodes (LEDs). LEDs are becoming increasingly important, in for example, automobile lighting, traffic signals, general lighting, and liquid crystal display (LCD) backlighting and display screens. Nanoparticle-based light-emitting devices have been made by embedding semiconductor nanoparticles in an optically clear (or sufficiently transparent) LED encapsulation medium, typically a silicone or an acrylate, which is then placed on top of a solid-state LED. The use of semiconductor nanoparticles potentially has significant advantages over the use of the more conventional phosphors. For example, semiconductor nanoparticles provide the ability to tune the emission wavelength of a LED. Semiconductor nanoparticles also have strong absorption properties and low scattering when the nanoparticles are well dispersed in a medium. The nanoparticles may be incorporated into an LED encapsulating material. It is important that the nanoparticles be well dispersed in the encapsulating material to prevent loss of quantum efficiency. Methods developed to date are problematic because the nanoparticles tend to agglomerate when formulated into LED encapsulants, thereby reducing the optical performance of the nanoparticles. Moreover, even after the nanoparticles have been incorporated into the LED encapsulant, oxygen can still migrate through the encapsulant to the surfaces of the nanoparticles, which can lead to photo-oxidation and, as a result, a drop in quantum yield (QY).

A nanoparticle's compatibility with a medium as well as the nanoparticle's susceptibility to agglomeration, photo-oxidation and/or quenching, is mediated largely by the surface composition of the nanoparticle. The coordination about the final inorganic surface atoms in any core, core-shell or core-multi shell nanoparticle is incomplete, with highly reactive "dangling bonds" on the surface, which can lead to particle agglomeration. This problem is overcome by passivating (capping) the "bare" surface atoms with protecting organic groups, referred to herein as capping ligands or a capping agent. The capping or passivating of particles not only prevents particle agglomeration from occurring. The capping ligand also protects the particle from its surrounding chemical environment and provides electronic stabilization (passivation) to the particles, in the case of core material. The capping ligand is usually a Lewis base bound to surface metal atoms of the outer most inorganic layer of the particle. The nature of the capping ligand largely determines the compatibility of the nanoparticle with a particular medium. These capping ligands are usually hydrophobic (for example, alkyl thiols, fatty acids, alkyl phosphines, alkyl phosphine oxides, and the like). Thus, the nanoparticles are typically dispersed in hydrophobic solvents, such as toluene, following synthesis and isolation of the nanoparticles. Such capped nanoparticles are typically not dispersible in more polar media.

The most widely used procedure to modify the surface of nanoparticles is known as ligand exchange. Lipophilic ligand molecules that coordinate to the surface of the nanoparticle during core synthesis and/or shelling procedures may subsequently be exchanged with a polar/charged ligand compound. An alternative surface modification strategy intercalates polar/charged molecules or polymer molecules with the ligand molecules that are already coordinated to the surface of the nanoparticle. Current ligand exchange and intercalation procedures may render the nanoparticle more compatible with aqueous media but usually result in materials of lower quantum yield (QY) and/or substantially larger size than the corresponding unmodified nanoparticle.

Thus, there is a need in the art for nanoparticles that are compatible with a variety of media and for techniques for modifying the surface of nanoparticles to render desired compatibility while maintaining the integrity and photophysical properties of the nanoparticle.

The subject matter of the present disclosure is directed to overcoming, or at least reducing the effects of, one or more of the problems set forth above.

SUMMARY OF THE DISCLOSURE

The present disclosure provides methods for modifying the surface of nanoparticles and of producing surface-functionalized nanoparticles. In general, the method includes associating a first type of molecule, referred to herein as a ligand interactive agent, with the surface of the nanoparticle. The ligand interactive agent is then reacted with a linking/crosslinking agent. The linking/crosslinking agent can serve two purposes: (1) it provides crosslinking between the molecules of the ligand interactive agent (and potentially also crosslinking between other ligands on the nanoparticle surface), and (2) it provides an anchor point for one or more surface modifying ligands.

The ligand interactive agent may associate with the surface of the nanoparticle via one or more of several different modes. For example, the ligand interactive agent may associate with the surface of the nanoparticle by intercalating with ligands, such as capping ligands, already present on the nanoparticle surface. The ligand interactive agent my associate with the nanoparticle surface via ligand exchange with such existing ligands. The ligand interactive agent may, or may not, include one or more functional groups that have affinity for the nanoparticle surface. One or more of these modes of interaction between the ligand interactive agent and the nanoparticle surface may be operative at a given time.

The ligand interactive agent includes one or more functional groups that interact with a linking/crosslinking agent. A linking/crosslinking agent provides crosslinking between molecules of the ligand interactive agent on the nanoparticle surface. Thus, the linking/crosslinking agent becomes incorporated into the ligand shell of the nanoparticle. The linking/crosslinking agent may have specific affinity for, or reactivity with, functional groups of the ligand interactive agent and may bridge between such functional groups. The linking/crosslinking agent may be multi-dentate and may bridge between two, three, or more ligands on the nanoparticles surface.

Crosslinking may increase the stability and robustness of the ligand shell of the nanoparticle. As a result, the nanoparticle may be less susceptible to degradation, quenching, photo-bleaching, and the like.

An initiator or catalyst may be used to initiate or facilitate crosslinking. The initiator or catalysts may be a chemical initiator, such as an acid, for example. The initiator may be a photo-initiator.

The linking/crosslinking agent may also serve as an attachment point for a surface modifying ligand. The surface modifying ligand may incorporate functionality that modifies the compatibility of the surface-modified nanoparticle with particular solvents or media. For example, the surface modifying ligand may incorporate polar groups, increasing the compatibility of the surface-modified nanoparticle with polar solvents, such as water, alcohols, ketones, ink resins, epoxy resins, and polar acrylate resins. As another example, the surface modifying ligand may comprise a silicone, or the like, increasing the compatibility of the surface modified nanoparticle with a silicone matrix. Particular ligand interactive agents, linking/crosslinking agents, and surface modifying ligands are discussed in more detail below.

According to one embodiment, the ligand interactive agent is first associated with the surface of the nanoparticle. The nanoparticle is then reacted with the linking/crosslinking agent and the surface modifying agent to effect crosslinking and binding of the surface modifying agent to the nanoparticle.

According to another embodiment, the surface modifying ligand is pre-associated with the ligand interactive agent. The nanoparticle is exposed to the ligand interactive agent/surface modifying ligand combination which associates to the surface of the nanoparticle. The nanoparticle is then exposed to the linking/crosslinking agent to effect crosslinking.

The foregoing summary is not intended to summarize each potential embodiment or every aspect of the present disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
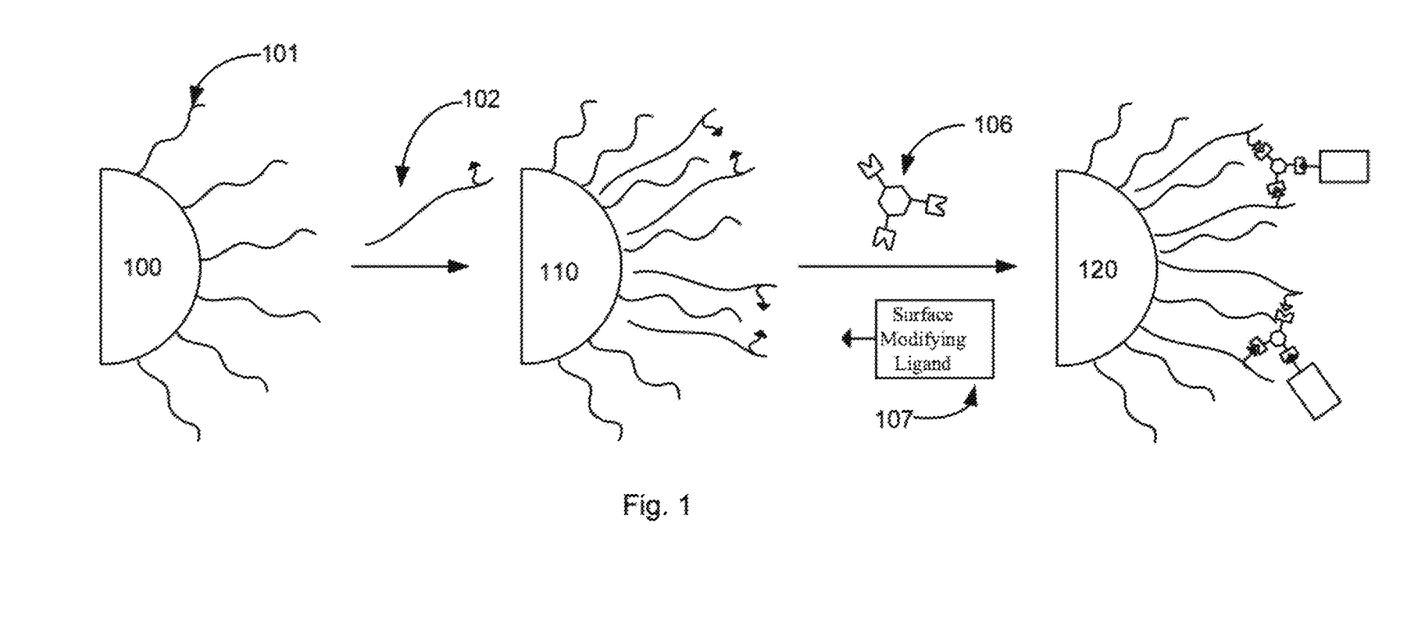
FIG. 1 is a schematic illustration of a method of modifying the surface of a nanoparticle.

FIG. 1 schematically illustrates an embodiment of a method of producing surface modified nanoparticles. A nanoparticle 100 includes a shell of organic ligands 101 associated with the surface of the nanoparticle. The instant disclosure is not limited to any particular type of nanoparticle. Nanoparticles of metal oxides (for example, iron oxides, magnetic nanoparticles, titanium oxides, zinc oxide, zirconium oxide, aluminum oxide), gold nanoparticles and silver nanoparticles can be all treated and surface-modified using the methods described herein. In preferred embodiments, the nanoparticle may include a semiconductor material, preferably a luminescent semiconductor material. The semiconductor material may incorporate ions from any one or more of groups 2 to 16 of the periodic table, and may include binary, ternary and quaternary materials, that is, materials incorporating two, three or four different ions respectively. By way of example, the nanoparticle may incorporate a semiconductor material, such as, but not limited to, CdS, CdSe, CdTe, ZnS, ZnSe, ZnTe, InP, InAs, InSb, AlP, AlS, AlAs, AlSb, GaN, GaP, GaAs, GaSb, PbS, PbSe, Si, Ge and combinations thereof. According to various embodiments, nanoparticles may have diameters of less than around 100 nm, less than around 50 nm, less than around 20 nm, less than around 15 nm and/or may be in the range of around 2 to 10 nm in diameter.

Nanoparticles that include a single semiconductor material, e.g., CdS, CdSe, ZnS, ZnSe, InP, GaN, etc. may have relatively low quantum efficiencies because of non-radiative electron-hole recombination that occurs at defects and dangling bonds at the surface of the nanoparticles. In order to at least partially address these issues, the nanoparticle cores may be at least partially coated with one or more layers (also referred to herein as "shells") of a material different than that of the core, for example a different semiconductor material than that of the "core." The material included in the, or each, shell may incorporate ions from any one or more of groups 2 to 16 of the periodic table. When a nanoparticle has two or more shells, each shell may be formed of a different material. In an exemplary core/shell material, the core is formed from one of the materials specified above and the shell includes a semiconductor material of larger band-gap energy and similar lattice dimensions as the core material. Exemplary shell materials include, but are not limited to, ZnS, ZnO, MgS, MgSe, MgTe and GaN. An exemplary multi-shell nanoparticle is InP/ZnS/ZnO. The confinement of charge carriers within the core and away from surface states provides nanoparticles of greater stability and higher quantum yield.

While the disclosed methods are not limited to any particular nanoparticle material, an advantage of the disclosed methods is that the methods can be used to modify the surface of cadmium-free nanoparticles, that is, nanoparticles comprising materials that do not contain cadmium. It has been found that it is particularly difficult to modify the surface of cadmium-free nanoparticles. Cadmium-free nanoparticles readily degrade when prior art methods, such as prior art ligand exchange methods, are used to modify the surface of such cadmium-free nanoparticles. For example, attempts to modify the surface of cadmium-free nanoparticles have been observed to cause a significant decrease in the luminescence quantum yield (QY) of such nanoparticles. The disclosed methods, on the other hand, provide surface-modified cadmium-free nanoparticles with high QY. For example, the disclosed methods have resulted in cadmium-free nanoparticles that are dispersible in water and which have QY greater than about 20%, greater than about 25%, greater than about 30%, greater than about 35%, and greater than about 40%. Examples of cadmium free nanoparticles include nanoparticles comprising semiconductor materials, e.g., ZnS, ZnSe, ZnTe, InP, InAs, InSb, AlP, AlS, AlAs, AlSb, GaN, GaP, GaAs, GaSb, PbS, PbSe, Si, Ge, and particularly, nanoparticles comprising cores of one of these materials and one or more shells of another of these materials.

Typically, as a result of the core and/or shelling procedures employed to produce the core, core/shell or core/multishell nanoparticles, the nanoparticles are at least partially coated with a surface binding ligand 101, such as myristic acid, hexadecylamine and/or trioctylphosphineoxide. Such ligands are typically derived from the solvent in which the core and/or shelling procedures were carried out. While ligands 101 of this type can increase the stability of the nanoparticles in non-polar media, provide electronic stabilization and/or negate undesirable nanoparticle agglomeration, as mentioned previously, such ligands typically prevent the nanoparticles from stably dispersing or dissolving in more polar media, such as aqueous solvents.

Figure 2:
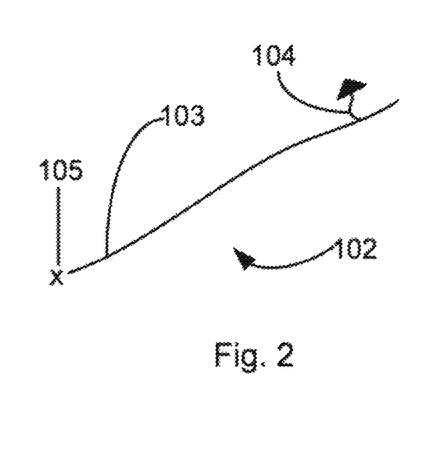
FIG. 2 is a schematic illustration of a ligand interactive agent.

As a first step of modifying nanoparticle 100, the nanoparticle is exposed to ligand interactive agent 102 to effect the association of ligand interactive agent 102 and the surface of nanoparticle 100. A schematic of ligand interactive agent 102 is shown in more detail in FIG. 2. Ligand interactive agent can comprise a chain portion 103 and a functional group 104 having a specific affinity for, or reactivity with, a linking/crosslinking agent, as described below. Examples of such functional groups 104 include nucleophiles such as thio groups, hydroxyl groups, carboxamide groups, ester groups, and a carboxyl groups. An ester is an example of such a functional group 104. Chain portion 103 may be, for example, an alkane chain. Ligand interactive agent 102 may, or may not, also comprise a moiety 105 having an affinity for the surface of a nanoparticle. Examples of such moieties 105 include thiols, amines, carboxylic groups, and phosphines. If ligand interactive group 102 does not comprise such a moiety 105, ligand interactive group can associate with the surface of nanoparticle 100 by intercalating with capping ligands 101 (see FIG. 1). Examples of ligand interactive agents 102 include $C_{8-20}$ fatty acids and esters thereof, such as isopropyl myristate.

Referring back to FIG. 1, it should be noted that ligand interactive agent 102 may be associated with nanoparticle 100 simply as a result of the processes used for the synthesis of the nanoparticle, obviating the need to expose nanoparticle 100 to additional amounts of ligand interactive agent 102. In such case, there may be no need to associate further ligand interactive agent with the nanoparticle. Alternatively, or in addition, nanoparticle 100 may be exposed to ligand interactive agent 102 after nanoparticle 100 is synthesized and isolated. For example, nanoparticle 100 may be incubated in a solution containing ligand interactive agent 102 for a period of time. Such incubation, or a portion of the incubation period, may be at an elevated temperature to facilitate association of ligand interactive agent 102 with the surface of nanoparticle 100. Associating ligand interactive agent 102 with nanoparticle 100 yields ligand interactive agent-nanoparticle association complex 110.

Following association of ligand interactive agent 102 with the surface of nanoparticle 100, the nanoparticle is exposed to linking/crosslinking agent 106 and surface modifying ligand 107. Linking/crosslinking agent 106 includes functional groups having specific affinity for groups 104 of ligand interactive agent 102. Linking/crosslinking agent 106 also has specific reactivity with surface modifying ligand 107. Thus, linking/crosslinking agent 106 may serve to crosslink the ligand shell of nanoparticle 100 and also may serve to bind surface modifying ligand 107 to the surface of nanoparticle 100.

Ligand interactive agent-nanoparticle association complex 110 can be exposed to linking/crosslinking agent 106 and surface modifying ligand 107 sequentially. For example, nanoparticle 100 (including 102) might be exposed to linking/crosslinking agent 106 for a period of time to effect crosslinking, and then subsequently exposed to surface modifying ligand 107 to incorporate 107 into the ligand shell of nanoparticle 100. Alternatively, nanoparticle 100 may be exposed to a mixture of 106 and 107, effecting crosslinking and incorporating surface modifying ligand in a single step.

Examples of suitable linking/crosslinking agents include any agent that will crosslink molecules of ligand interactive agent 102 and provide a binding site for surface modifying ligand 107. Particularly suitable linking/crosslinking agents 106 comprise melamine-based compounds:

A particularly suitable melamine-based linking/crosslinking agent is hexamethoxymethylmelamine (HMMM):

HMMM is commercially available from Cytec Industries, Inc. (West Paterson, N.J.) as CYMEL303. HMMM can react in an acid-catalyzed reaction to crosslink various functional groups, such as amides, carboxyl groups, hydroxyl groups, and thiols. In the presence of strong acid, HMMM crosslinks thiol-containing compounds at temperatures above about 75° C. and crosslinks carboxyl- or amide-containing compounds at temperatures above about 130° C. These temperatures are not intended to be limiting; lower temperatures, such as about 120° C., may result in crosslinking at a slower rate. An embodiment disclosed herein is a composition comprising a nanoparticle and a melamine compound, such as HMMM. The composition may comprise a polar solvent. The composition may be an ink formulation.

The presence of a strong proton acid is typically needed to catalyze crosslinking with HMMM. The most active catalysts are those with the lowest pKa values. Examples of catalysts include mineral acids, p-toluene sulfonic acid, dinonylnapthalene disulfonic acid, dodecylbenzene sulfonic acid, oxalic acid, maleic acid, hexamic acid, phosphoric acid, alkyl phosphate ester, phthalic acid, acrylic acid, and salicylic acid.

Referring back to FIG. 1, surface modifying ligand 107 is associated with nanoparticle 100 by binding to ligand interactive agent 102. Surface modifying ligand 107 can modify the compatibility of the nanoparticle with a particular solvent or media. For example, associating surface modifying ligand 107 with nanoparticle 100 may render nanoparticle 100 soluble, or at least more compatible, with aqueous solvents. Examples of such surface modifying ligands include polyethers, such as polyethylene glycols. One example of a surface modifying ligand 107 is hydroxyl-terminated polyethylene glycol. Other surface modifying ligands can be selected to impart compatibility with other media or solvents. For example, a silicone-based surface modifying ligand, such as polydimethysiloxane (PDMS) can be used as a surface modifying ligand to impart compatibility of the nanoparticle with silicone resins and polycarbonate resins. As another example, guaifenesin can be used to impart compatibility with polar solvents and polar acrylates, such as trimethylopropane trimethacrylate (TMPTM).

An embodiment as illustrated in FIG. 1 can be summarized as follows: Nanoparticle 100, incorporating capping ligand 101 is incubated in an appropriate solvent with ligand interactive agent 102 to effect association of 102 with the surface of nanoparticle 100. Linking/crosslinking agent 106, surface modifying ligand 107, and an initiator or catalyst are added and the entire mixture is heated together at a time and temperature sufficient to effect crosslinking and association of surface modifying ligand into the ligand shell of nanoparticle 100.

Figure 3:
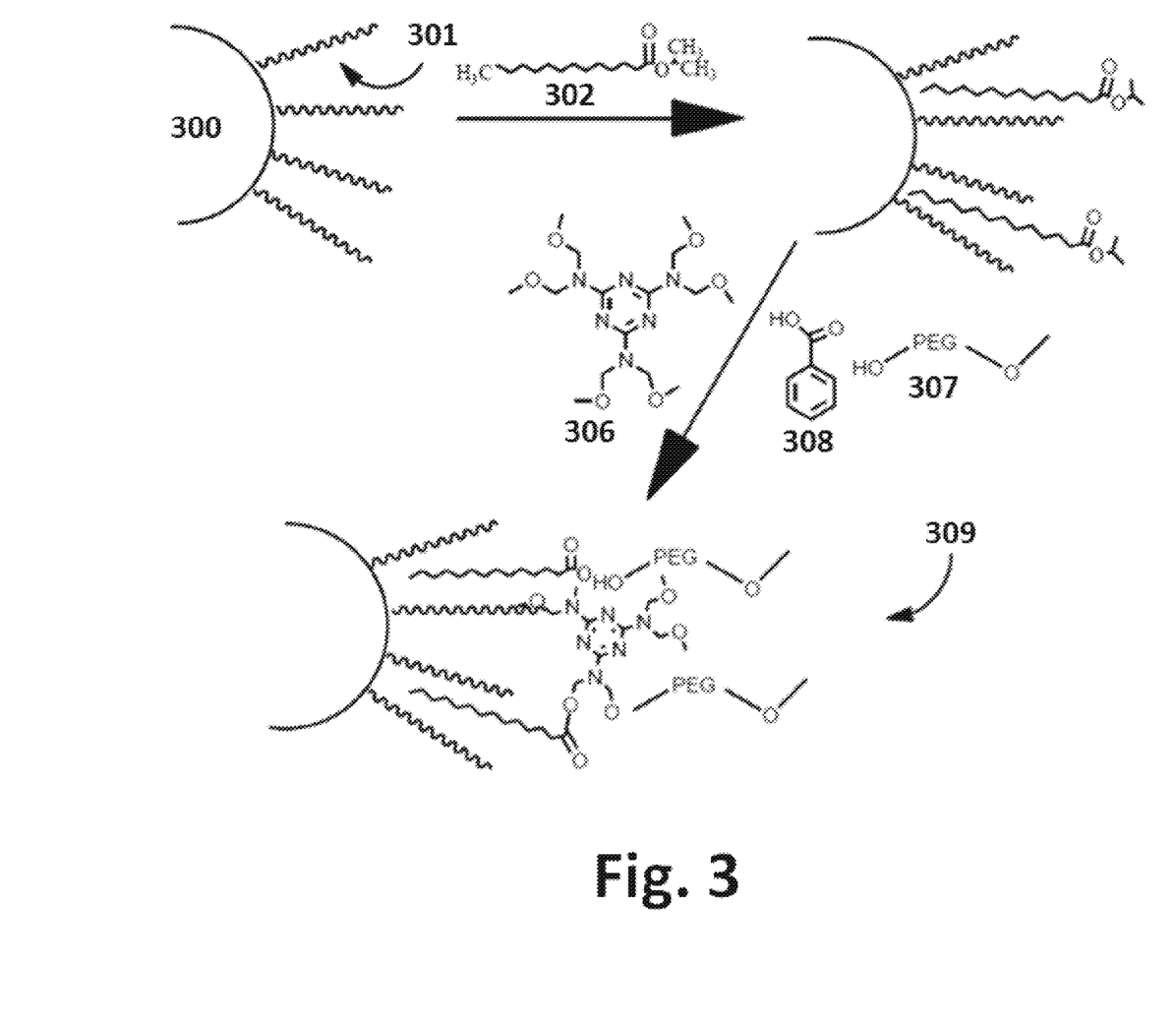
FIG. 3 illustrates a method of modifying the surface of a nanoparticle using isopropyl myristate as a ligand interactive agent, HMMM as a linking/crosslinking agent, and PEG as a surface modifying ligand.

FIG. 3 illustrates an embodiment wherein nanoparticle 300, including capping ligand 301 is exposed to isopropyl myristate as a ligand interactive agent 302. According to the embodiment illustrated in FIG. 3, the isopropyl myristate associates with the surface of the nanoparticle 300 by intercalating with the capping ligand. Such intercalation can be effected by incubating the nanoparticle and the isopropyl myristate in a solvent, such as toluene for a period of time ranging from several minutes to several hours. According to one embodiment, the nanoparticle and isopropyl myristate are heated in toluene to about 50-60° C. for about 5 minutes and then left at room temperature overnight. According to one embodiment, about 200 mg of nanoparticles can be incubated with about 100 microliters of isopropyl myristate.

According to the embodiment illustrated in FIG. 3, HMMM is provided as a linking/crosslinking agent 306, salicylic acid as a catalyst 308, and monomethoxy polyethylene oxide (mPEG) as surface modifying ligand 307. A mixture of HMMM, salicylic acid, and mPEG in toluene can be added to the nanoparticle mixture and heated to about 140° C. for a period of time ranging from about several minutes to several hours to yield PEG-modified nanoparticle 309.

The embodiment illustrated in FIG. 3 results in a PEG-modified nanoparticle that is compatible with an aqueous dispersant. The surface modifying ligand can be tailored to provide compatibility with other media. As mentioned above, a silicone-based surface modifying ligand, such as polydimethylsiloxane (PDMS) can be used as a surface modifying ligand to impart compatibility of the nanoparticle with silicone resins and polycarbonate resins. As another example, guaifenesin can be used to impart compatibility with polar solvents and polar acrylates, such as trimethylolpropane trimethacrylate (TMPTM). Generally, any surface modifying ligand that is reactive with HMMM and soluble in toluene can be used in the embodiment illustrated in FIG. 3.

Figure 4:
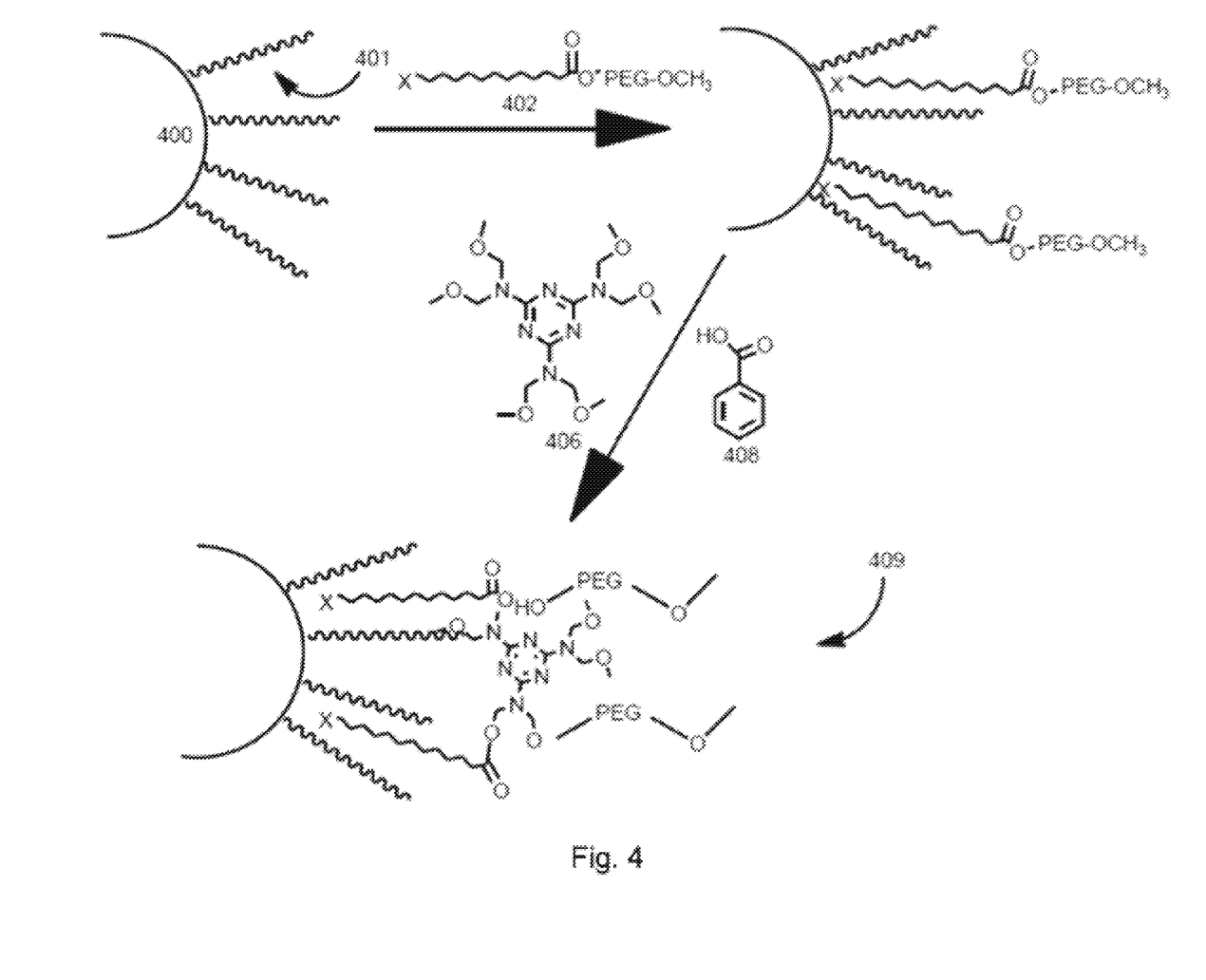
FIG. 4 illustrates a method of modifying the surface of a nanoparticle with a PEG-modified myristate surface modifying ligand.

FIG. 4 illustrates an alternative embodiment wherein nanoparticle 400, including capping ligand 401, is treated with a surface modifying ligand 402 that includes a functional group (an ester group) that is capable of reacting with HMMM linking/crosslinking agent 406. Surface modifying ligand 402 is a myristate-based ligand that includes a functional group (PEG-OCH$_3$) that imparts water solubility to nanoparticle 400. Surface modifying ligand 402 may also include a functional group (denoted "X" in the embodiment illustrated in FIG. 4) that has a specific affinity for the surface of nanoparticle 400. Examples of such functional groups include thiols and carboxylic groups.

Once surface modifying ligand is associated with the surface of nanoparticle 400, nanoparticle 400 is then reacted with linking/crosslinking agent 406 and catalyst 408 to effect crosslinking between surface modifying ligands 402. HMMM is the linking/crosslinking agent 406 and salicylic acid is the catalyst 408 in the embodiment illustrated in FIG. 4. Crosslinking the surface modifying ligands increases the stability of the ligand shell of the surface-modified nanoparticle 409.

EXAMPLES

1. Silicone-Compatible Nanoparticles.

Cadmium free quantum dot nanoparticles (CFQD) (InP/ZnS) (200 mg) with red emission at 608 nm was dispersed in toluene (1 mL) with isopropyl myristate (100 microliters). The mixture was heated at 50° C. for about 1-2 minutes then slowly shaken for 15 hours at room temperature. A toluene solution (4 mL) of HMMM (Cymel 303) (400 mg), monohydroxy polydimethyl siloxane (MW5kD) (200 mg), and p-toluene sulfonic acid (70 mg) was added to the nanoparticle dispersion. The mixture was degassed and refluxed at 140° C. for 4 hours while stirring at 300 rpm with a magnetic stirrer. During the first hour a stream of nitrogen was passed through the flask to ensure the removal of volatile byproducts generated by the reaction of HMMM with nucleophiles. The mixture was allowed to cool to room temperature and stored under inert gas. The surface-modified nanoparticles showed little or no loss in fluorescence quantum yield and no change in the emission peak or full width at half max (FWHM) value, compared to unmodified nanoparticles. The surface-modified nanoparticles dispersed well in PDMS polymers of variable molecular weight (from 10 to 1000 kD) and remained dispersed even after removing residual toluene. In contrast, the same concentration of unmodified nanoparticles dispersed in PDMS aggregated and separated out of the host silicone.

The films were prepared as follows: nanoparticles (6 mg) dispersed in toluene (~200 microliters) were mixed well with of PDMS resin (1 g) using a spatula. The mixture was vigorously degassed under vacuum for several hours to remove toluene. The mixture then was mounted on a glass slide to form a film.

Figure 5A:
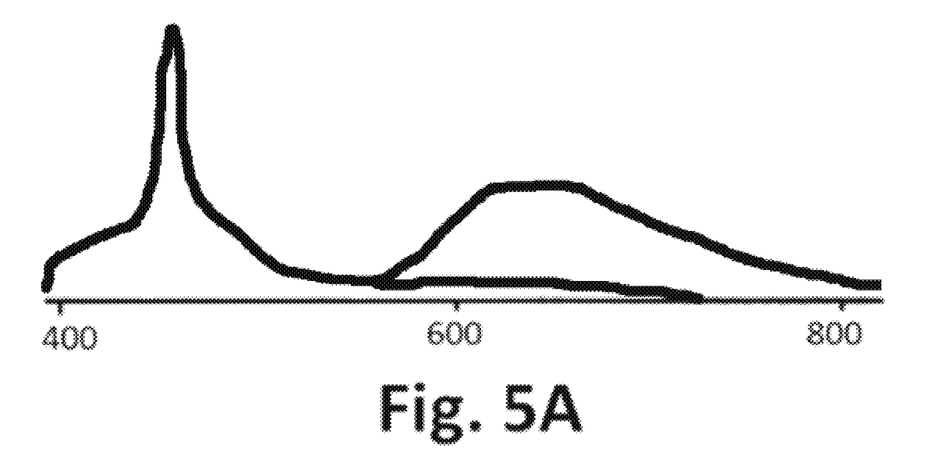
FIG. 5A shows the fluorescence spectrum of silicone-compatible nanoparticles suspended in PDMS.
Figure 5B:
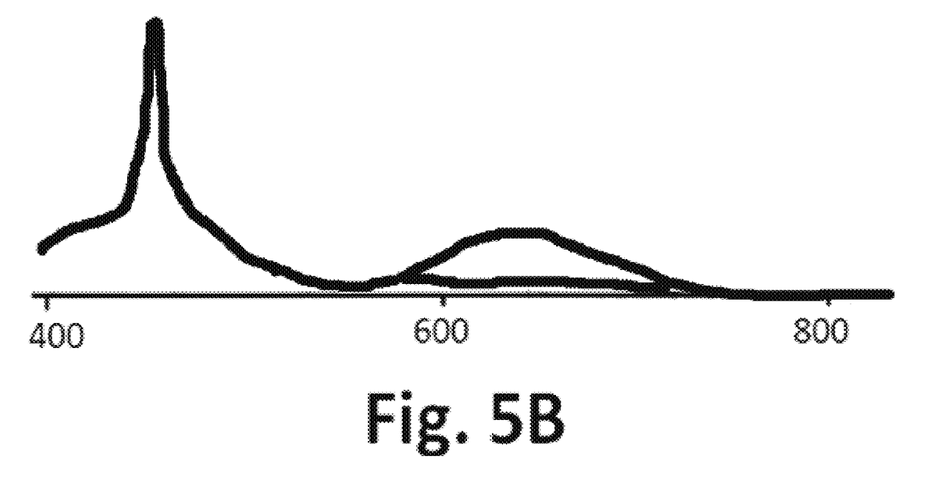
FIG. 5B shows the fluorescence spectrum of unmodified nanoparticles suspended in PDMS.

FIGS. 5A and 5B illustrate fluorescence spectra of surface modified nanoparticles and unmodified nanoparticles suspended in PDMS, respectively. For each of FIGS. 5A and 5B, four measurements were performed: one measurement of a blank sample with internal standard only and three measurements of the nanoparticles suspended in PDMS. The fluorescence quantum yield of the surface-modified nanoparticles (QY=59%) is greater than that of the unmodified nanoparticles (QY=56%). The quantum yield of the unmodified nanoparticles is decreased due to extensive aggregation and reabsorption effects.

2. Epoxy-Compatible Nanoparticles.

Cadmium free quantum dot nanoparticles (CFQD) (InP/ZnS) (200 mg) with green emission at 525 nm was dispersed in toluene (1 mL) with isopropyl myristate (100 microliters). The mixture was heated at 50° C. for about 1-2 minutes then slowly shaken for 15 hours at room temperature. A toluene solution (4 mL) of HMMM (Cymel 303) (400 mg), trimethylolpropane triglycidyl ether (200 mg) and salicylic acid (70 mg) was added to the nanoparticle dispersion. The mixture was degassed and refluxed at 140° C. for 4 hours while stirring at 300 rpm with a magnetic stirrer. During the first hour a stream of nitrogen was passed through the flask to ensure the removal of volatile byproducts generated by the reaction of HMMM with nucleophiles. The mixture was allowed to cool to room temperature and stored under inert gas. The surface-modified nanoparticles showed little or no loss in fluorescence quantum yield and no change in the emission peak or full width at half max (FWHM) value, compared to unmodified nanoparticles. The surface-modified nanoparticles dispersed well in in epoxide polymers of variable molecular weight and remained dispersed even after removing residual toluene. In contrast, the same concentration of unmodified nanoparticles aggregated and separated out of the host matrix.

Figure 6A:
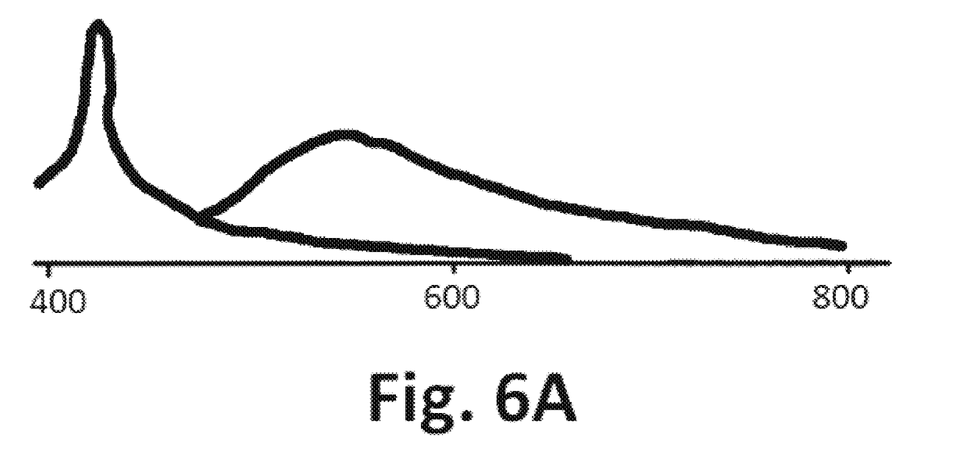
FIG. 6A shows the fluorescence spectrum of epoxy-compatible nanoparticles suspended in epoxy resin.
Figure 6B:
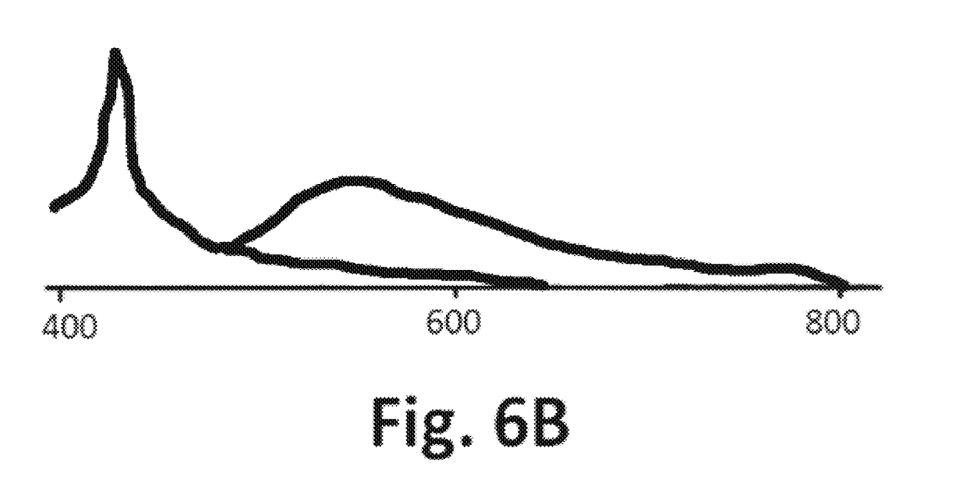
FIG. 6B shows the fluorescence spectrum of unmodified nanoparticles suspended in epoxy resin.

FIGS. 6A and 6B illustrate fluorescence spectra of surface modified nanoparticles and unmodified nanoparticles suspended in EX135 epoxy resin, respectively. For each of FIGS. 6A and 6B, four measurements were performed: one measurement of a blank sample with internal standard only and three measurements of the nanoparticles suspended in epoxy resin. The fluorescence quantum yield of the surface-modified nanoparticles (QY=60%) is greater than that of the unmodified nanoparticles (QY=58%). The quantum yield of the unmodified nanoparticles is decreased due to extensive aggregation and re-adsorption effects.

Polystyrene-Compatible Nanoparticles.

Cadmium free quantum dot nanoparticles (CFQD) (InP/ZnS) (200 mg) with red emission at 608 nm was dispersed in toluene (1 mL) with isopropyl myristate (100 microliters). The mixture was heated at 50° C. for about 1-2 minutes then slowly shook for 15 hours at room temperature. A toluene solution (4 mL) of HMMM (Cymel 303) (400 mg), monomethoxy polyethylene oxide ($CH_3O$-PEG2000-OH) (400 mg), and salicylic acid (50 mg) was added to the nanoparticle dispersion. The mixture was degassed and refluxed at 130° C. for 2 hours while stirring at 300 rpm with a magnetic stirrer. During the first hour a stream of nitrogen was passed through the flask to ensure the removal of volatile byproducts generated by the reaction of HMMM with nucleophiles. The mixture was allowed to cool to room temperature and stored under inert gas. The surface-modified nanoparticles showed little or no loss in fluorescence quantum yield and no change in the emission peak or full width at half max (FWHM) value, compared to unmodified nanoparticles. When an aliquot of the modified dots was mixed with polystyrene or polystyrene copolymer resins (5% solids in toluene, e.g., styrene-ethylene/butylene-styrene or styrene-ethylene/propylene-styrene (SEPS, SEBS, Kraton) the modified nanoparticles dispersed very well in the host polystyrene resins and stayed dispersed even after removing the residual toluene. At the same concentration of nanoparticles, the unmodified crude nanoparticles aggregated and separated out of the host resin. The film of the surface-modified nanoparticle is uniform, whereas the film of the unmodified nanoparticle shows significant aggregation of nanoparticles.

3. Water-Compatible Nanoparticles.

Cadmium free quantum dot nanoparticles (CFQD) (InP/ZnS/ZnO) (200 mg) with red emission at 608 nm was dispersed in toluene (1 mL) with isopropyl myristate (100 microliters). The mixture was heated at 50° C. for about 1-2 minutes then slowly shook for 15 hours at room temperature. A toluene solution (4 mL) of HMMM (Cymel 303) (400 mg), monomethoxy polyethylene oxide ($CH_3O$-PEG2000-OH) (400 mg), and salicylic acid (50 mg) was added to the nanoparticle dispersion. The mixture was degassed and refluxed at 140° C. for 4 hours while stirring at 300 rpm with a magnetic stirrer. During the first hour a stream of nitrogen was passed through the flask to ensure the removal of volatile byproducts generated by the reaction of HMMM with nucleophiles. The mixture was allowed to cool to room temperature and stored under inert gas. The surface-modified nanoparticles showed little or no loss in fluorescence quantum yield and no change in the emission peak or full width at half max (FWHM) value, compared to unmodified nanoparticles.

An aliquot of the surface-modified nanoparticles was dried under vacuum and deionized water was added to the residue. The surface modified nanoparticles dispersed well in the aqueous media and remained dispersed permanently. In contrast, unmodified nanoparticles could not be suspended in the aqueous medium.

Figure 7:
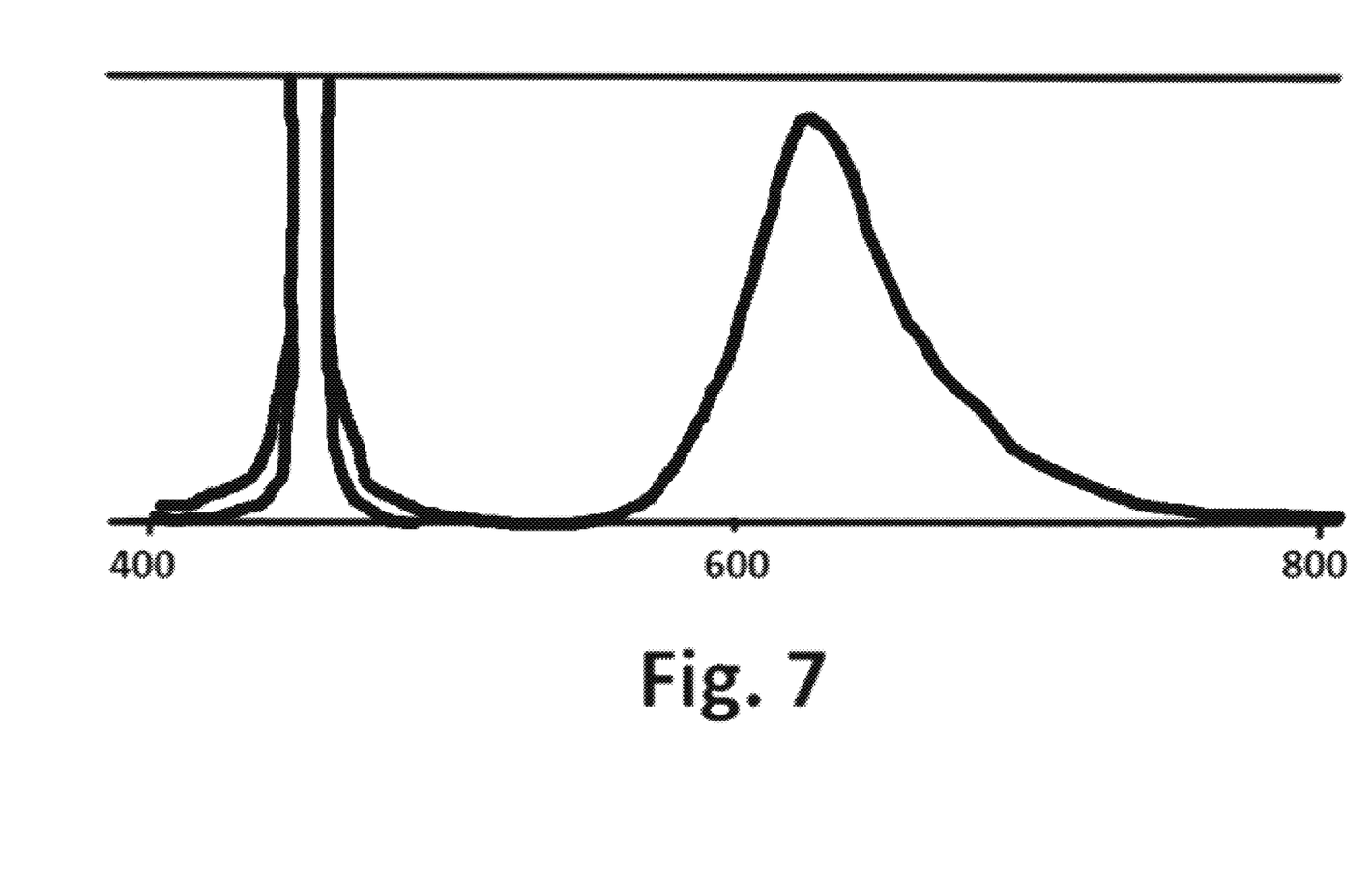
FIG. 7 shows a fluorescence spectrum of water soluble nanoparticles in water.

FIG. 7 shows fluorescence spectrum of the surface-modified nanoparticles in water. Four measurements were performed: one measurement of a blank sample with internal standard only and three measurements of the nanoparticles suspended in epoxy resin. The fluorescence quantum yield of the surface-modified nanoparticles is 47. It is noteworthy that traditional methods for modifying nanoparticles to increase their water solubility (e.g., ligand exchange with mercapto-functionalized water soluble ligands) are ineffective under mild conditions to render the nanoparticles water soluble. Under harsher conditions, such as heat and sonication, the fraction that becomes water soluble has very low quantum yield (QY<20%). The instant method, in contrast, provides water soluble nanoparticles with a high quantum yield.

Surface-modified nanoparticles prepared as in this example also disperse well and remain permanently dispersed in other polar solvents, including ethanol, propanol, acetone, methylethylketone, butanol, tripropylmethylmethacrylate, or methylmethacrylate.

4. LED Stabilization and Brightness Enhancement.

Figure 8A:
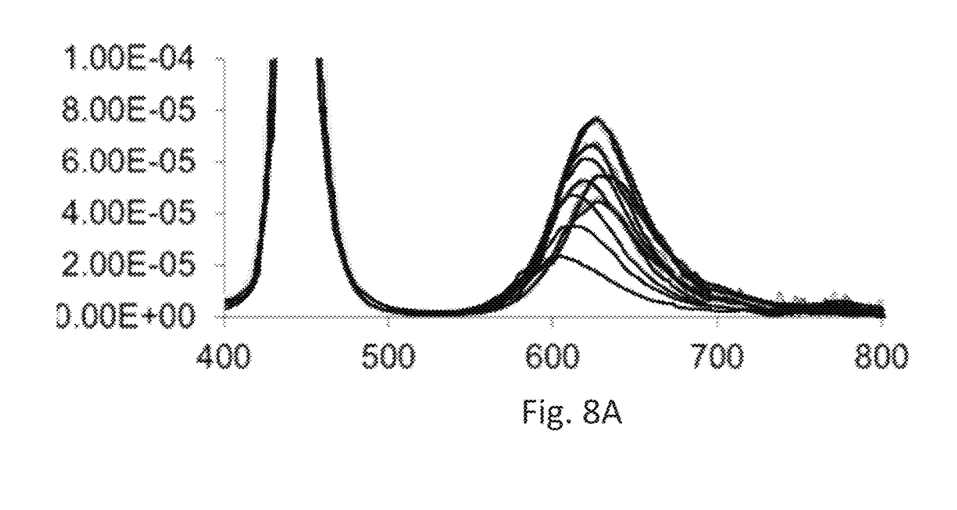
FIG. 8A shows the emission spectrum of an LED incorporating epoxy-compatible nanoparticles suspended in an epoxy encapsulant.
Figure 8B:
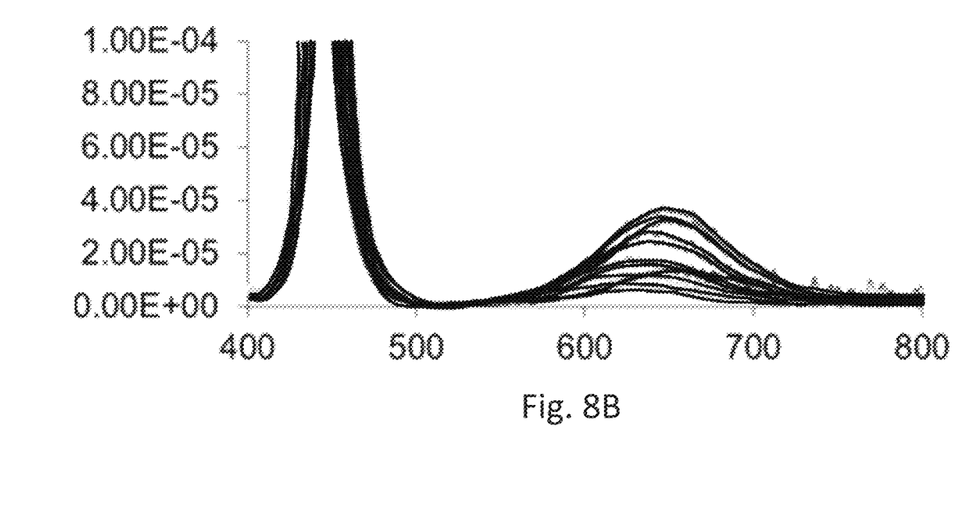
FIG. 8B shows the emission spectrum of an LED incorporating unmodified nanoparticles encapsulated in acrylate beads suspended in epoxy.

Epoxy-compatible nanoparticles were prepared as described in Example 2. The epoxy-compatible nanoparticles were added to LED epoxy encapsulant (EX135). LEDs were prepared using the encapsulant and blue-emitting LED chips. FIG. 8A illustrates emission curves of an LED incorporating the surface-modified nanoparticles. Emission measurements were taken every daily for one week and then weekly. For comparison, FIG. 8B illustrates emission curves of an LED incorporating unmodified nanoparticles. The unmodified nanoparticles were first incorporated into acrylate beads, which were then encapsulated in epoxy. As expected, the emission intensity of both LEDs decays over time as the LEDs degrade. However, the absolute emission intensity of the LED incorporating the surface-modified nanoparticles is about twice the intensity of the LED incorporating the unmodified nanoparticles.

Figure 9:
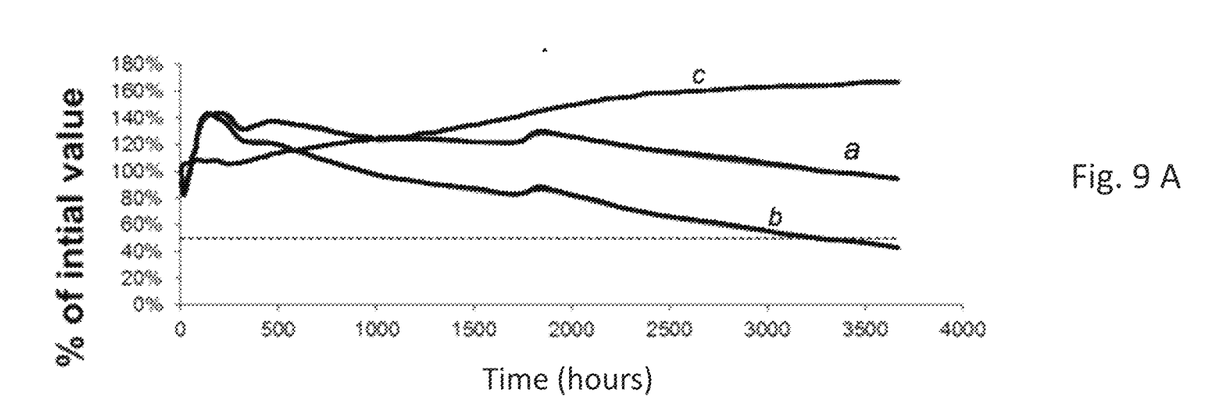
FIG. 9A shows stability measurements of an LED incorporating epoxy-compatible nanoparticles suspended in an epoxy encapsulant.
FIG. 9B shows stability measurements of an LED incorporating unmodified nanoparticles encapsulated in acrylate beads suspended in epoxy.

FIGS. 9 A and 9 B show the percent efficacy a, percent emission intensity b, and percent LED intensity c as a function of time for the LEDs incorporating the surface modified and the unmodified nanoparticles, respectively. Percent efficacy is a measure of light brightness based on human eye sensitivity. Percent emission intensity is a measure of the intensity of the emission peak. Percent LED intensity is a measure of the blue LED chip intensity. The data illustrated in FIGS. 9 A and 9 B indicate that LED incorporating surface-modified nanoparticles have comparable LED stability compared to the LED incorporating unmodified nanoparticle embedded in highly crosslinked polymer beads. Incorporating the nanoparticles in highly crosslinked beads and then encapsulating the resulting beads in an LED encapsulant (e.g., EX135) is effective for maximizing the stability of the nanoparticles. However, LED devices using encapsulated beads suffer from loss of brightness due to the beads' fabrication chemistry as well as to the high rate of light scattering by the beads in the light path. The LED using the surface-modified nanoparticles achieve comparable LED stability to the encapsulated bead LED but has an absolute emission intensity that is about twice the intensity of the LED incorporating unmodified nanoparticles.

The foregoing description of preferred and other embodiments is not intended to limit or restrict the scope or applicability of the inventive concepts conceived of by the Applicants. It will be appreciated with the benefit of the present disclosure that features described above in accordance with any embodiment or aspect of the disclosed subject matter can be utilized, either alone or in combination, with any other described feature, in any other embodiment or aspect of the disclosed subject matter.

In exchange for disclosing the inventive concepts contained herein, the Applicants desire all patent rights afforded by the appended claims. Therefore, it is intended that the appended claims include all modifications and alterations to the full extent that they come within the scope of the following claims or the equivalents thereof.

What is claimed is:

1. A surface-modified nanoparticle comprising:
   a ligand interactive agent-nanoparticle association complex;
   a linking/crosslinking agent bound to a ligand interactive agent of the ligand interactive agent-nanoparticle association complex; and
   a surface modifying ligand bound to the linking/crosslinking agent, the surface modifying ligand is a monomethoxy polyethylene oxide, a monohydroxy polydimethylsiloxane, trimethylolpropane triglycidyl ether, a polyether, or guaifenesin.

2. The surface-modified nanoparticle of claim 1, wherein a nanoparticle of the ligand interactive agent-nanoparticle association complex comprises a metal oxide.

3. The surface-modified nanoparticle of claim 2, wherein the metal oxide is selected from the group consisting of an iron oxide, titanium oxide, zinc oxide, zirconium oxide, and aluminum oxide.

4. The surface-modified nanoparticle of claim 1, wherein a nanoparticle of the ligand interactive agent-nanoparticle association complex comprises a metal.

5. The surface-modified nanoparticle of claim 4, wherein the metal is gold or silver.

6. The surface-modified nanoparticle of claim 1, wherein a nanoparticle of the ligand interactive agent-nanoparticle association complex comprises a semiconductor material.

7. The surface-modified nanoparticle of claim 6, wherein the semiconductor material is selected from the group consisting of CdS, CdSe, CdTe, ZnS, ZnSe, ZnTe, InP, InAs, InSb, AlP, AlS, AlAs, AlSb, GaN, GaP, GaAs, GaSb, PbS, PbSe, Si, Ge, and any combination thereof.

8. The surface-modified nanoparticle of claim 1, wherein a nanoparticle of the ligand interactive agent-nanoparticle association complex is a core/shell nanoparticle.

9. The surface-modified nanoparticle of claim 8, wherein the core/shell nanoparticle has two or more shells.

10. The surface-modified nanoparticle of claim 1, wherein the linking/crosslinking agent is a melamine-based compound.

11. The surface-modified nanoparticle of claim 1, wherein the ligand interactive agent comprises any one of a thiol moiety, an amine moiety, a carboxylic acid moiety and a phosphine moiety.

12. The surface-modified nanoparticle of claim 1, wherein the ligand interactive agent is a $C_8$-$C_{20}$ fatty acid.

13. The surface-modified nanoparticle of claim 1, wherein the ligand interactive agent is a $C_8$-$C_{20}$ fatty acid ester.

14. A surface-modified nanoparticle comprising:
   a ligand interactive agent-nanoparticle association complex;
   a melamine-based compound bound to a ligand interactive agent of the ligand interactive agent-nanoparticle association complex; and
   a surface modifying ligand bound to the melamine-based compound.

15. The surface-modified nanoparticle of claim 14, wherein the surface modifying ligand is a monomethoxy polyethylene oxide, a monohydroxy polydimethylsiloxane, trimethylolpropane triglycidyl ether, a polyether, or guaifenesin.

16. The surface-modified nanoparticle of claim 14, wherein a nanoparticle of the ligand interactive agent-nanoparticle association complex comprises a metal, a metal oxide, or a semiconductor material.

17. The surface-modified nanoparticle of claim 14, wherein the ligand interactive agent comprises any one of a thiol moiety, an amine moiety, a carboxylic acid moiety and a phosphine moiety.

18. The surface-modified nanoparticle of claim 14, wherein the ligand interactive agent is a $C_8$-$C_{20}$ fatty acid or a $C_8$-$C_{20}$ fatty acid ester.

19. The surface-modified nanoparticle of claim 14, wherein the surface modifying ligand is configured to render the surface-modified nanoparticle compatible with a host material.

20. A surface-modified nanoparticle comprising:
   a ligand interactive agent-nanoparticle association complex comprising a nanoparticle, the nanoparticle comprising gold or silver;
   a linking/crosslinking agent bound to a ligand interactive agent of the ligand interactive agent-nanoparticle association complex; and
   a surface modifying ligand bound to the linking/crosslinking agent.

* * * * *